(12) United States Patent
Dewaele et al.

(10) Patent No.: US 10,542,878 B2
(45) Date of Patent: Jan. 28, 2020

(54) GUIDE FOR STEERING WIRES FOR A STEERING MECHANISM FOR A STEERABLE TOOL

(71) Applicant: Steerable Instruments NV, Sint-Denijs-Westrem (BE)

(72) Inventors: Frank Dewaele, De Pinte (BE); Cyriel Mabilde, Oudenaarde (BE); Bart Blanckaert, Eeklo (BE); Alain Kalmar, Ghent (BE); Lieven Maene, Knokke-Heist (BE)

(73) Assignee: Steerable Instruments NV, Sint-Denijs-Westrem (BE)

( * ) Notice: Subject to any disclaimer, the term of this patent is extended or adjusted under 35 U.S.C. 154(b) by 212 days.

(21) Appl. No.: 15/528,779

(22) PCT Filed: Dec. 8, 2015

(86) PCT No.: PCT/EP2015/078932
§ 371 (c)(1),
(2) Date: May 23, 2017

(87) PCT Pub. No.: WO2016/091856
PCT Pub. Date: Jun. 16, 2016

(65) Prior Publication Data
US 2018/0146841 A1    May 31, 2018

(30) Foreign Application Priority Data
Dec. 8, 2014    (EP) .................................. 14196793

(51) Int. Cl.
*A61B 1/05*    (2006.01)
*A61B 1/005*   (2006.01)
(Continued)

(52) U.S. Cl.
CPC .......... *A61B 1/0055* (2013.01); *A61B 1/0057* (2013.01); *A61M 25/0147* (2013.01); *A61B 2017/003* (2013.01); *A61M 25/0136* (2013.01)

(58) Field of Classification Search
CPC ... A61B 1/0052; A61B 1/0055; A61B 1/0056; A61B 1/0057; A61B 1/008; A61B 1/01;
(Continued)

(56) References Cited

U.S. PATENT DOCUMENTS

| 429,095 A | 5/1890 | Livingstone |
| 2,290,842 A | 7/1942 | Bush |

(Continued)

FOREIGN PATENT DOCUMENTS

| DE | 196 08 809 A1 | 9/1997 |
| EP | 0 301 288 A1 | 2/1989 |
| WO | 2006057702 A2 | 6/2006 |

OTHER PUBLICATIONS

PCT International Search Report and Written Opinion dated Mar. 16, 2016 for PCT International Patent Application No. PCT/EP2015/078932, 14 pages.

(Continued)

*Primary Examiner* — Thomas M McEvoy
(74) *Attorney, Agent, or Firm* — Amster, Rothstein & Ebenstein LLP

(57) ABSTRACT

The invention relates to a longitudinal member, LM, guide (300) for guiding a set of LMs (110) for a mechanical transmission system, MTS, (100) for a steerable tool (500), which LM guide (300) comprises a body (302) having a proximal side (342), a distal side (344) and an outside edge (316), wherein the body (302) of the LM guide (300) comprises a set of channels (310) arranged around a fictive tube (320), each channel (310) passing from the proximal side (342) to the distal side (344) of the body (302), (Continued)

configured to retain an LM (110) of the set in a fixed radial position around the fictive tube (32), being connected to the outside edge (316) of the body (302) via a slot (314), wherein the slot has a width (326) narrower than the channel (310) width (320).

15 Claims, 8 Drawing Sheets

(51) Int. Cl.
*A61M 25/01* (2006.01)
*A61B 17/00* (2006.01)

(58) Field of Classification Search
CPC ........ A61B 1/0051; A61B 2017/00314; A61B 2017/00318; A61B 2017/00323; A61M 25/0147; A61M 2025/015
See application file for complete search history.

(56) References Cited

U.S. PATENT DOCUMENTS

| | | | |
|---|---|---|---|
| 4,873,965 A | 10/1989 | Danieli | |
| 5,438,975 A * | 8/1995 | Miyagi | ............. A61B 1/00071 600/109 |
| 5,656,011 A * | 8/1997 | Uihlein | .................. A61B 1/008 600/143 |
| 5,783,312 A | 7/1998 | Laughman et al. | |
| 2005/0107667 A1 | 5/2005 | Danitz et al. | |
| 2008/0262538 A1 | 10/2008 | Danitz et al. | |
| 2009/0227842 A1 * | 9/2009 | Ando | .................. A61B 1/0055 600/146 |
| 2010/0261964 A1 | 10/2010 | Danitz et al. | |
| 2010/0261971 A1 | 10/2010 | Danitz et al. | |
| 2010/0262075 A1 | 10/2010 | Danitz et al. | |
| 2010/0262161 A1 | 10/2010 | Danitz et al. | |
| 2010/0262180 A1 | 10/2010 | Danitz et al. | |
| 2013/0340559 A1 | 12/2013 | Danitz et al. | |

OTHER PUBLICATIONS

PCT Written Opinion of the International Preliminary Examining Authority dated Dec. 13, 2016 for PCT International Patent Application No. PCT/EP2015/078932, 8 pages.
PCT Notification Concerning Transmittal of International Preliminary Report on Patentability of the International Searching Authority, dated Apr. 4, 2017 in connection with PCT International Patent Application No. PCT/EP2015/078932, 9 pages.
Amended Claims dated Feb. 13, 2017 in connection with PCT International Patent Application No. PCT/EP2015/078932, 11 pages.

* cited by examiner

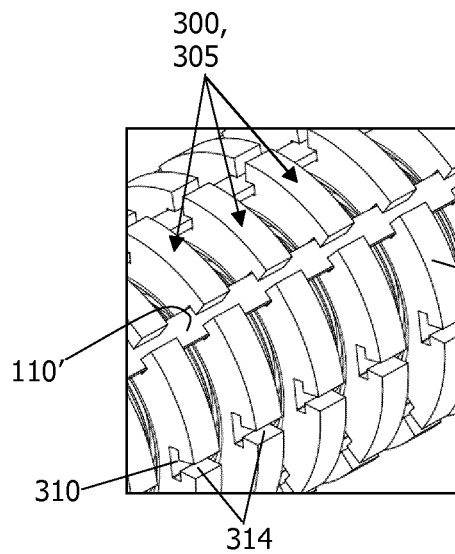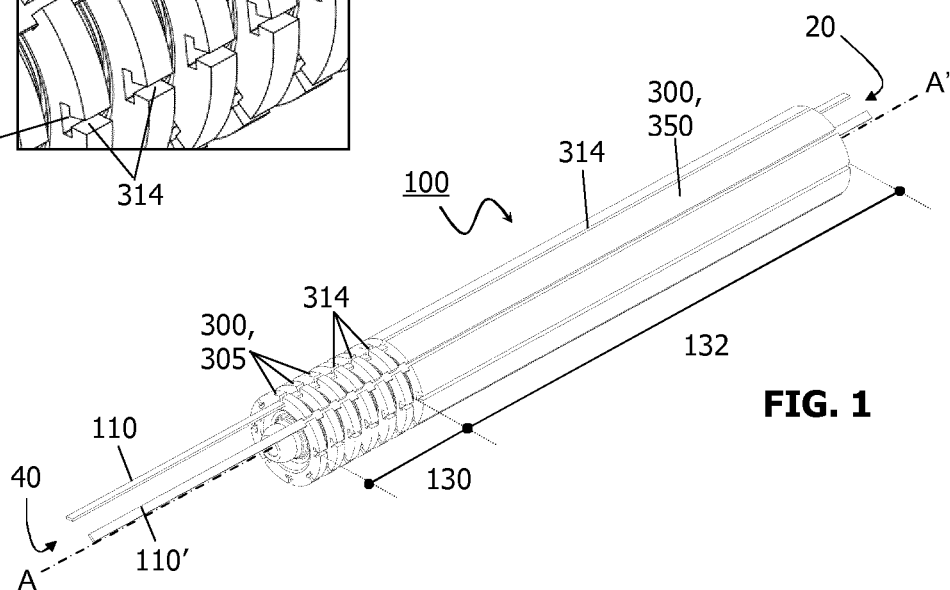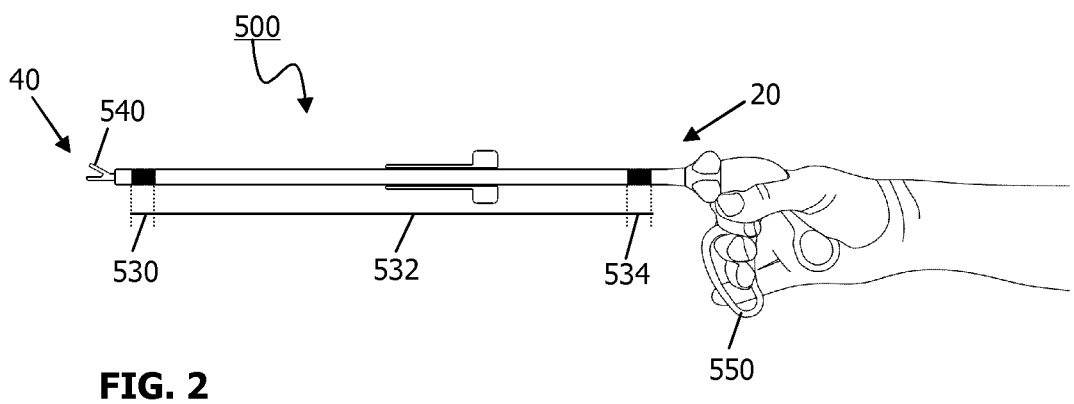

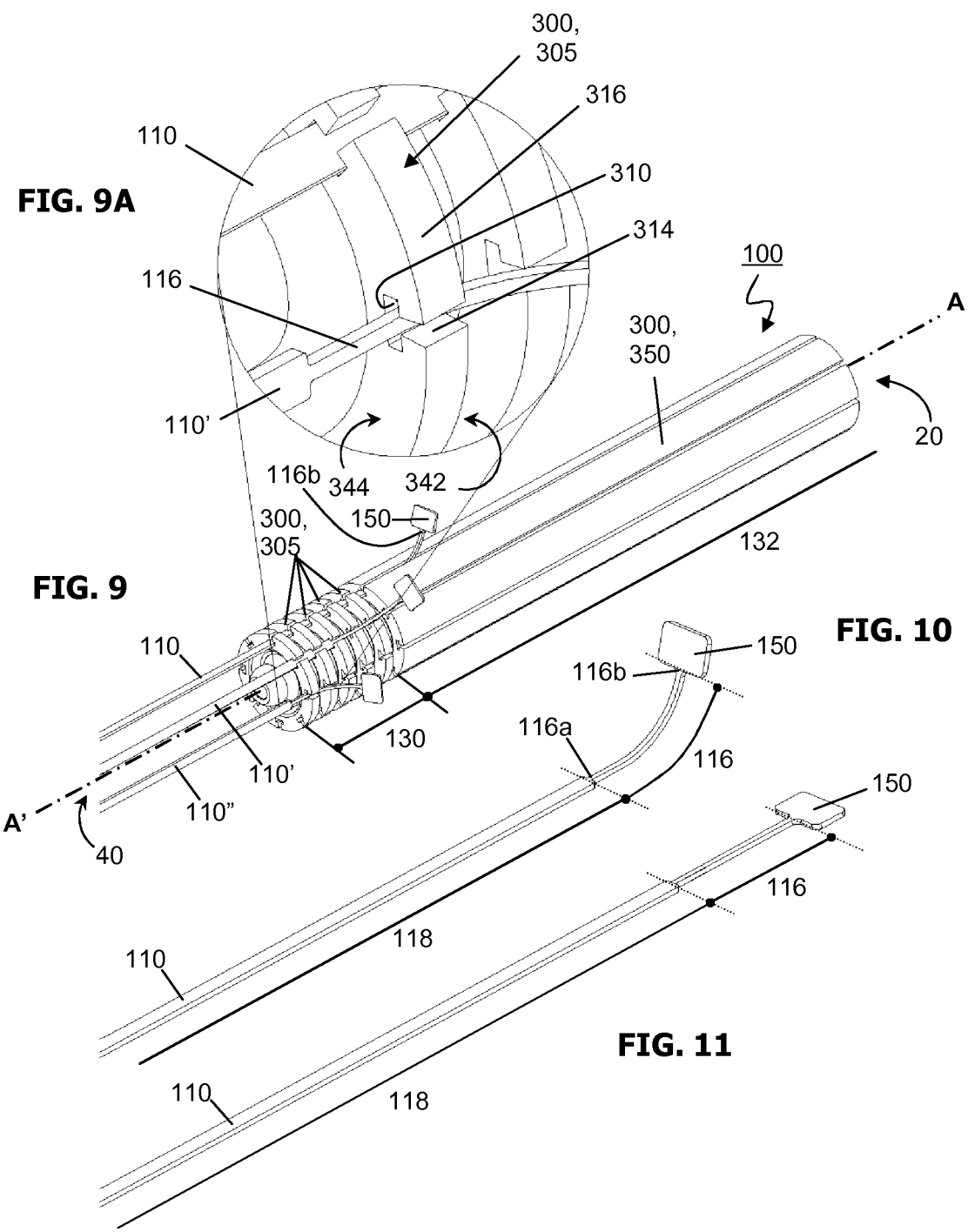

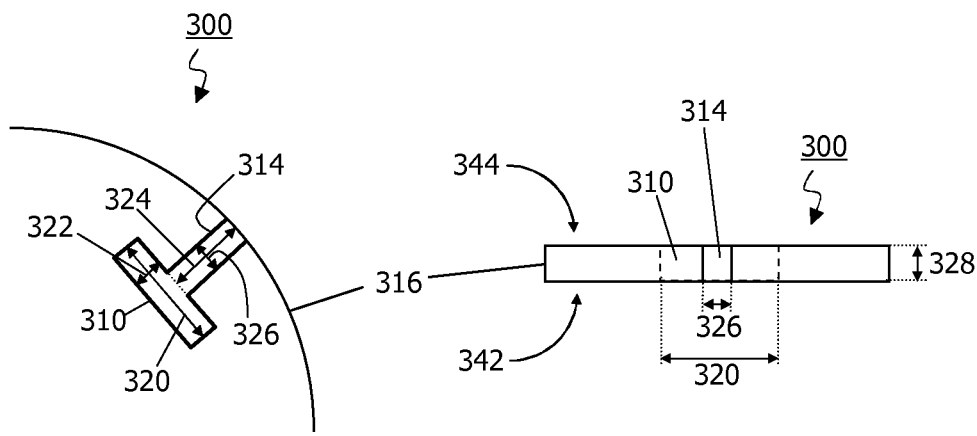
FIG. 12A  FIG. 12B
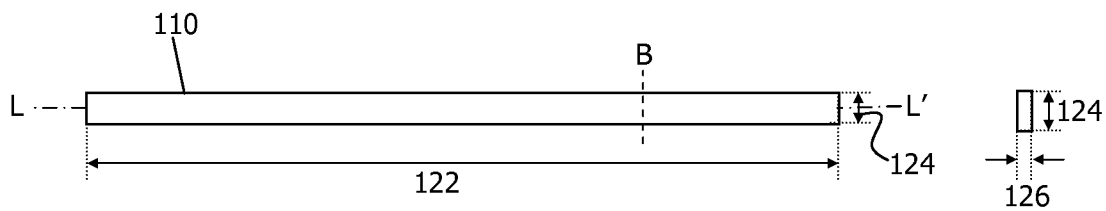
FIG. 13A  FIG. 13B
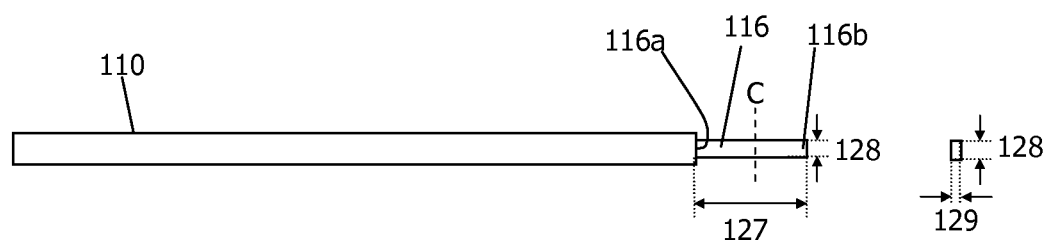
FIG. 14A  FIG. 14B
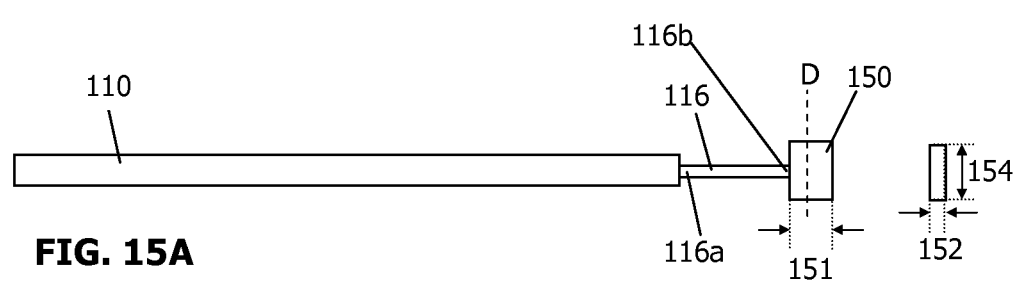
FIG. 15A  FIG. 15B

GUIDE FOR STEERING WIRES FOR A STEERING MECHANISM FOR A STEERABLE TOOL

CROSS-REFERENCE TO RELATED APPLICATIONS

This application is a U.S. national stage entry under 35 U.S.C. § 371 of PCT International Patent Application No. PCT/EP2015/078932, filed Dec. 8, 2015, which claims priority to European Patent Application No. 14196793.5, filed Dec. 8, 2014, the contents of which are incorporated herein by reference in their entirety.

BACKGROUND TO THE INVENTION

Surgery is characterized by a continuous search towards minimal invasiveness. Since the 1980s open surgery has been largely replaced by an endoscopic approach in which long instruments are inserted through trocars in a carbon dioxide-extended abdomen. Laparoscopic surgery, known for its validated benefits of shorter hospitalization, less postoperative pain and earlier recovery, is more demanding for the surgeon. Precise dissection, suturing and knot tying in minimal access surgery is an advanced skill. Especially when the suture line and the axis of the needle holder are unparallel this skill is difficult to master. Recent steps in the evolution towards minimal invasiveness are Single Port Surgery (SPS) and Natural Orifice Transluminal Endoscopic Surgery (NOTES). Both approaches result in a scarless healing. In SPS the instruments are inserted through one big trocar through e.g. the umbillicus.

A disadvantage of endoscopic surgery is reduced dexterity for the surgeon. This is mainly because of the fulcrum effect and the absence of wrist like movements at the tip of the instrument. Awareness of this disadvantage increases as more complex endoscopic procedures and single port surgeries (characterized by sword fighting of the instruments) are performed.

The fulcrum effect is explained by the long instruments that pivot at the level of the trocar inserted in the abdomen. A movement of the handle to the left is translated in a movement to the right at the effector (e.g. a pair of scissors). It is surprising to see how quickly a surgeon can adapt to these inversed movements.

The lack of wrist-like movements is more difficult to overcome. A state-of-the-art solution is provided by the surgical robot. In this master slave system the movements of the surgeon's hands at the console are transferred to fluent movements at the instrument's tip. This solution is quite expensive, leading to the development of cheaper hand instruments with an omni-directional articulated tip Most of the challenge is explained by the reduced dexterity. A conventional rigid laparoscopic instrument offers only 4 degrees of freedom (rotation, up/down angulations, left/right angulations, in/out movements).

To overcome this restriction in movements, various designs for steerable instruments have been developed. In its simplest form an articulated instruments consist of a prebent flexible tube sliding out of a rigid straight tube (uni-directional articulated instruments). This tip can only bend in one direction and cannot withstand an appropriate amount of lateral force. More advanced alternatives are instruments that allow bending movements of the tip in one plane. Because of the nature of the construction, a mostly stable tip is created. These bi-directional instruments need to be navigated to a point of interest by bending into one direction and then by turning the whole instrument around its own axis. This is not intuitive. True wrist movements are only possible with omni-directional systems. The omnidirectional articulated instruments consist mainly of a proximal and distal end, a proximal and distal bending part and an intermediate portion in between. Movement of the proximal end is transferred to a movement at the distal end. Examples are described in U.S. Pat. Nos. 7,410,483 and 8,105,350.

Similar to robotic surgery, omni-directional articulated instruments provide 7 degrees of freedom (axial rotation and deflection of the tip in two planes are added to the 4 DOF of conventional rigid instruments). A combination of up/down and left/right movements at the proximal side allows to reach any point at the distal effector side without the need for a rotation around its own axis.

The increased manoeuvrability is paid back by a serious decrease in tip stability. To solve this, hybrid solutions such as the Kymerax® system (Terumo) and Jaimy® system (EndoControl) compensate by using strong electrical motors to restore the tip stability.

Omni-directional articulated instruments offer, in comparison to robotic systems the advantages of low costs and tactile feedback.

A problem in the art of omni-directional articulated instruments is in the assembly thereof. The steering wires are required to be narrow so as to be able to maximise the number of wires which leads to a smoother steering. Threading thin wires into a steerable tube housing may present a problems of pushability since the thin wire is prone to buckling, and the problem of friction increases the further the wire is inserted into the tube. With a steerable tube of 30 cm of more in length, insertion of each wire by this method is time consuming. An alternative problem is how to assemble a robust steerable tube, particularly where the end of the steering wires need to be secured around an annular ring to provide push/pulling forces to the wires. Welding the ends to the annular ring can produce weaknesses, is time consuming, and leads to an increased diameter of the instrument. The use of adhesive relies on a strong bond between the elements; the forces exerted and daily instrument use can cause one of more wires to slidably detach from the annular ring. A pre-attached annular ring is impossible to thread into an instrument. The present invention provides a solution to one or more of these problems.

SOME EMBODIMENTS OF THE INVENTION

One aspect of the invention present invention relates to a longitudinal member, LM, guide (300) for guiding a set of LMs (110) for a mechanical transmission system, MTS, (100) for a steerable tool (500), which LM guide (300) comprises a body (302) having a proximal side (342), a distal side (344) and an outside edge (316), wherein the body (302) of the LM guide (300) comprises a set of channels (310) arranged around a fictive tube (320), each channel (310) passing from the proximal side (342) to the distal side (344) of the body (302), configured to retain an LM (110) of the set in a fixed radial position around the fictive tube (32), being connected to the outside edge (316) of the body (302) via a slot (314), wherein the slot has a width (326) narrower than the channel (310) width (320).

The number of channels (310) may be at least 4.

The MTS (100) may have a proximal end (20), a distal end (40), a transmission shaft region, TSR (132), and transmission bendable distal part (130, TBDP) adjacent to the TSR (132) that moves omnidirectionally responsive to actuation of the MTS (100) at the proximal end (20), wherein the MTS comprises:

a set of longitudinal members, LMs (110), configured to transmit actuating movement along the TSR (132) to the TBDP (130), a set of LM guides (300) as defined above, wherein each LM (110) is inserted into a channel (310) of the set of channels of an LM guide (300) such that they are arranged around the fictive tube (320) in a fixed radial position.

At least two of the LM guides (300) in the set may be articulated LM guides (305) tandemly arranged in the TDBP (130) and are mutually articulated, thereby supporting omnidirectional bending of the LMs (110) in the TDBP (130).

The articulated LM guides (305) may be in pairwise mutual contact through a pivot joint.

At least two of the LM guides (300) in the set may be fixed LM guides (350) arranged in the TSR (132) and are rotationally fixed with respect to each other, or only one of the LM guides (300) in the set is a fixed LM guide (350) arranged in the TSR (132), and having a continuous body spanning the length of the TSR (132).

The MTS (100) may further comprise a transmission bendable proximal part, TBPP (134), for omnidirectional actuation by the user and which induces the omnidirectional movement response of the TBDP (130).

The combined transverse profile of the channel (310) and slot (314) in the body (302) of the LM guide (300) may be a T-shaped or mushroom-shape.

Each LM (110) may be disposed at one end with a longitudinal tail (116) having a trailing end (116a) at one end attached to the LM (110) and at the other end a leading end (116b), wherein at least the trailing end (116a) is configured for passage through the slot (314) of the LM guide (300).

The tail leading end (116b) may be disposed with an end stop (150) configured to limit entry of the tail leading end (116b) into the slot (314).

The leading ends (116b) of at least two tails (116) may be connected to a common end stop (150).

A non-tailed end of each LM (110) in the set may be attached to an anchoring tab (160) configured to limit entry of the LM (110) into the channel (310) of the LM guide (300).

The non-tailed ends of at least two LMs (116) may be connected to a common anchoring tab (160).

The TBDP (130) may be configured for movement in at least two different intersecting planes responsive to the movements of the TBPP (134), and wherein the MTS (100) is further provided with an end effector (540) at the distal end of the TBDP (130) wherein the MTS (100) is configured such that the end effector (540) is rotationally fixed in relation to the distal bending part TBDP (130), and the end effector (540) is rotatable when the TBDP (130) is in a bent position, by a complementary rotation of the TBPP (134).

Another aspect of the invention relates to an expandable planar sheet.

The expandable planar sheet (142) may be provided with a pattern of cuts arranged such that planar expansion of the sheet provides a longitudinal member, LM, assembly (140) having a set of LMs (110) arranged mutually parallel, each LM (110) attached at one end to a separate tail (116) wherein the tails (116) are each attached at their leading ends (116b) to a common end stop (150) that has an undulating pattern. The non-tailed end of each and every LM (110) may be each attached to a common anchoring tab (160). The common anchoring tab (160) may be non-expandable. The common anchoring tab (160) may be expandable and have an undulating pattern after expansion.

Another aspect of the invention relates to an expandable planar sheet provided with a pattern of cuts arranged such that planar expansion of the sheet provides an LM assembly having a set of LMs (110) arranged mutually parallel, each LM (110) attached at one end to a separate tail (116) wherein the tails (116) are each attached at their leading ends (116b) to a common end stop (150) that has an undulating pattern, and wherein the non-tailed end of each LM (110) is attached to a common anchoring tab (160) that has an undulating pattern.

The expandable planar sheet (142) may be configured such it has a greater width (e.g. maximum width) in an expanded state (142(b)). Each tail (116) may have a width less than the width of the attached LM (110). The common end stop (150) may comprise an array of "Y"s interconnected by the Y-arms in an expanded state (142(b)).

BRIEF DESCRIPTION OF THE FIGURES

FIG. 1 is an isometric view of a partial assembly process of a mechanical transmission system (MTS).

FIG. 1A is a detail of two longitudinal members (LMs) each fully housed in a channel accessed by a slot.

FIG. 2 is an isometric view of a steerable tool incorporating an MTS of the invention.

FIG. 9 is an isometric view of a partial assembly process of an MTS containing a set of tandemly arranged LM guides of the invention aligned such that the slots form an effective groove.

FIG. 9A shows a detail of an LM fully housed in a channel, and of an LM being guided into a channel by the tail, which tail passes through a slot.

FIG. 10 is an isometric view of an LM provided at one end with a tail bend upwards FIG. 11 is an isometric view of a LM provided at one end with a tail in a straight configuration.

FIGS. 12A and 12B show a channel and slot with dimensional indications.

FIGS. 13A and 13B show an LM, together with dimensional indications

FIGS. 14A and 14B show an LM disposed with a tail, together with dimensional indications.

FIGS. 15A and 15B show a plan view of a LM disposed with a tail and an end stop.

DETAILED DESCRIPTION OF INVENTION

Figure 3:
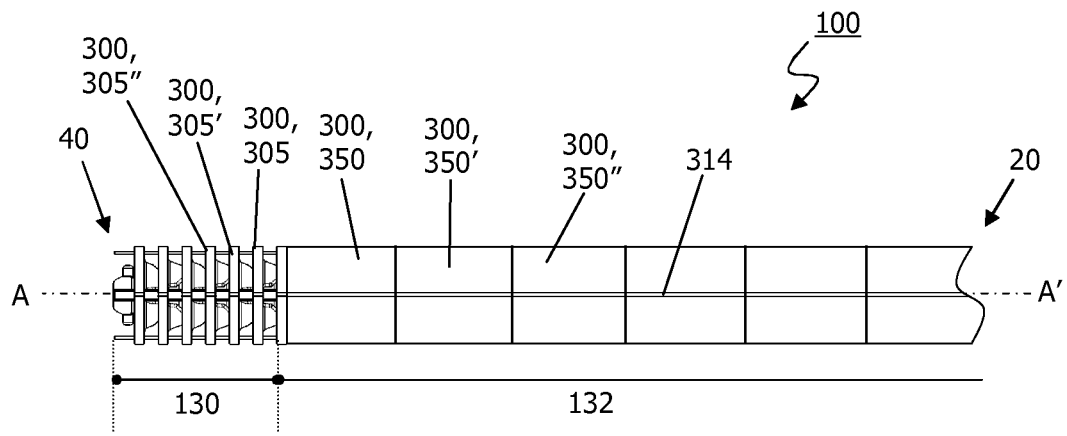
FIG. 3 depicts an outer view of an MTS containing longitudinal members (LM) guides of the invention.

Before the present method used in the invention is described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. All publications referenced herein are incorporated by reference thereto. All United States patents and patent applications referenced herein are incorporated by reference herein in their entirety including the drawings.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

The present invention relates to a guide for holding steering wires for a mechanical transmission system (MTS) for a steerable tool. The steering wires, known as longitudinal members, LM, herein, are maintained in a fixed radial position with respect to a central axis of the MTS, by LM guides which are mutually articulated at the bending end part of the mechanical transmission system (MTS) and hence of the steerable tool. The LM guide is disposed with a set of channels for holding the LMs in position. A channel is disposed with a slot connecting it to an outside edge of the LM guide. When the slots are aligned in a plurality of tandemly arranged LM guides, they effectively form a groove, and the LM can be advanced into the line of channels by applying a pulling force through the effective groove.

The steerable tool is preferably longitudinal, meaning it is longer in one direction. It does necessarily not imply the steerable tool is linear, though a linear (straight) steerable tool is within the scope of the invention. The steerable tool may be straight or curved, for instance, having a C- or S-shape shaft region.

Typically, a steerable tool has a proximal end and distal end and comprises a bendable distal part (BDP), sometimes known as a wrist, that moves responsive to actuation of the MTS at the proximal end. Actuation of the MTS at the proximal end induces a movement response in the BDP. The steerable tool is also provided with a shaft region, that may be essentially rigid or semi-rigid, one end of which is disposed with the BDP. The shaft region is longitudinal, meaning it is longer in one direction. It does necessarily not imply the shaft region is linear, though a linear (straight) shaft is within the scope of the invention. The shaft region may be straight or curved, for instance, having a C- or S-shape. To control BDP, steering wires which are known as longitudinal members (LMs) are used in the MTS. They control the BDP by pulling or pushing. The MTS comprises a set of longitudinal members (LM) each having a proximal end and a distal end, arranged in a longitudinal direction around a fictive tube. The tip (distal terminal end) of the BDP should be able to move with equal ease in any direction i.e. there is no singularity. The movement response is proportion to the degree of actuation.

The shaft region is preferably essentially rigid or semi-rigid, or may be flexible and become rigid or semi-rigid when co-operating with a rigid or semi-rigid exotube or outer tube. The shaft region is adjacent to the BDP. The shaft region may contact the BDP. The steerable tool may further be provided with a bendable proximal part (BPP) at the proximal end of the steerable tool. The BPP is adjacent to the shaft region i.e. the shaft region is disposed between the BDP and BPP. The shaft region may contact the BPP. Movement of the BPP actuates the MTS at the proximal end and induces a movement response in the BDP. Movement of BPP in different radial directions and to different bending degrees is transmitted using the MTS to the BDP, and results in a corresponding change in radial direction and/or degree of bending of the BDP. The steerable tool may be actuated at the proximal end using an electromechanical device connected directly to the MTS, for instance to two or more of the LMs, or each and every LM. Typically the LMs in the shaft region would be actuated. In such case, the tool may be devoid of a BPP. Alternatively, robotic control may be realised by using an electromechanical device to actuate the BPP. The electromechanical device may be, for instance, a servo motor. Coupling to an electromechanical device would facilitate direct integration into a surgical robot.

The movement response of the BDP may be:
 a change in degree of bending within a plane parallel to and contacting a central longitudinal axis of and extending from the shaft region,
 a change direction of the bend within a plane perpendicular to and contacting a central longitudinal axis of and extending from the shaft region.

The combination of movements the steerable tool allows would normally facilitate a rotation of the shaft region that could be transmitted to BDP at its tip while the BDP is in a bent position. However, the inventors have found that the tip of BDP does not rotate synchronously with the shaft region. There is a "dead-zone", backlash or play where torque applied at the proximal end and transmitted through the shaft region does not result in a rotation of the BDP tip, particularly when it is in a bent position.

The steerable tool may be a surgical instrument, such as, for instance, a laparoscopic instrument or an endovascular catheter. The invention can be used in an articulated instrument such as but not limiting to endovascular applications, surgical instruments, robotic tele-operated medical robotics or hand-held surgical tools and industrial applications.

The BDP is configured to move omni-directionally i.e. in any radial direction. BDP is preferably configured to move in any radial direction (about 360° with respect to central longitudinal axis (A'-A) of the shaft region). The BDP is preferably configured to move in at least two different planes (e.g. 3, 4, 5, 6, 7, 8 or more) disposed parallel to and contacting a central longitudinal axis (A'-A) of the shaft region. Preferably, the BDP is configured to move in an infinite number of different planes disposed parallel to and contacting a central longitudinal axis (A'-A) of the shaft region.

Similarly, the BPP, where present, is configured to move omni-directionally i.e. in any radial direction. BPP is preferably configured to move in any radial direction (about 360° with respect to central longitudinal axis (A'-A) of the shaft region). MTS is preferably configured to move the BPP in at least 8 different directions. The BPP is preferably configured to move in at least two different planes (e.g. 3, 4, 5, 6, 7, 8 or more) disposed parallel to and contacting a central longitudinal axis (A'-A) of the shaft region. Preferably, the BPP is configured to move in an infinite number of different planes disposed parallel to and contacting a central longitudinal axis of the shaft region.

The steerable tool may be provided with an end effector such as grip, pliers, cutting scissors and the like. The end effector is provided at the distal end of the steerable tool.

Furthermore it may be possible to rotate the distal tip of the instrument about its own axis even in a bent status. The steerable tool may be provided with an end effector at the distal end of the BDP wherein the MTS is configured such that the end effector is rotationally fixed in relation to the BDP, and the end effector is rotatable when the BDP is in a bent position, by a complementary rotation of the BPP. The end effector may be rotationally fixed in relation to the BDP by means of a lockable element configured to allow rotational adjustment of and to rotationally fix the end effector in rotational relation to the BDP.

The MTS as described herein has a proximal end and distal end. The distal end is provided with a transmission bendable distal part (TBDP) that that moves responsive to actuation of the MTS at the proximal end, and which moves the BDP of the steerable tool.

The TBDP corresponds in position with the BDP. Movements of the TBDP are transferred to the BDP of the steerable tool. The proximal end may be provided with a transmission bendable proximal part (TBPP). Movements by the user of the BPP of the steerable tool are transferred to the TBPP. The TBDP corresponds in position with the BPP. The TBPP actuates the MTS at the proximal end and induces the movement response of the TBDP that is transferred to the BDP of the steerable tool.

The MTS is also provided with a transmission shaft region (TSR) to be disposed within the corresponding shaft region of the steerable tool. The TSR is preferably essentially rigid or semi-rigid, or may become rigid or semi-rigid when co-operating with a rigid or semi-rigid exotube or outer tube.

The MTS may be actuated at the proximal end using an electromechanical device connected directly to the MTS, for instance to two or more of the LMs, or each and every LM. Typically the LMs in the LM shaft region would be actuated. In such case, the tool may be devoid of a TBPP. Alternatively, robotic control may be realised by using an electromechanical device to actuate the BPP. The electromechanical device may be, for instance, a servo motor. This would facilitate direct integration into a surgical robot.

The MTS is preferably configured to move the BDP omni-directionally. MTS is preferably configured to move the BDP in any direction (about 360° with respect to central longitudinal axis (A'-A) of the TSR). MTS is preferably configured to move the BDP in at least 8 different directions. The MTS may be configured to move the BDP in at least two different planes (e.g. 3, 4, 5, 6, 7, 8 or more) disposed parallel to and contacting a central longitudinal axis (A'-A) of the TSR. Preferably, MTS is configured to move the BDP in an infinite number of different planes disposed parallel to and contacting a central longitudinal axis (A'-A) of the transmission shaft region.

Furthermore it may be possible to rotate the distal tip of the instrument about its own axis even in a bent status. The MTS may be provided with an end effector at the distal end of the TBDP wherein the MTS is configured such that the end effector is rotationally fixed in relation to the TBDP, and the end effector is rotatable when the TBDP is in a bent position, by a complementary rotation of the TBPP. The end effector may be rotationally fixed in relation to the TBDP by means of a lockable element configured to allow rotational adjustment of and to rotationally fix the end effector in rotational relation to the TBDP.

The MTS comprises a set of longitudinal members (LMs) each having a proximal end and a distal end, arranged in a longitudinal direction around a fictive tube. The LMs are also known as steering wires. The fictive tube is a geometric shape around which the LMs are aligned. It is preferably longitudinal. The LMs contact the fictive tube. It preferably has a circular transverse-cross section, a transverse cross-section being essentially perpendicular to a longitudinal axis. A central axis (A'-A) of the fictive tube is preferably coaxial with a central axis of the steerable tool. The fictive tube is preferably cylindrical. The fictive tube has diameter that is smaller than the diameter of the steerable tool at the corresponding position.

The LM as described herein has a proximal end and distal end. The distal end is provided with a LM bendable distal part (LMBDP) to be disposed in the TBDP of the MTS. The LM is provided with a LM shaft region (LMSR) to be disposed in the corresponding TSR of the MTS. The LMSR is proximal to and adjacent to the LMBDP. The proximal end may be provided with a LM bendable proximal part (LMBPP) to be disposed in the TBPP of the MTS.

The ends of the LM are maintained in fixed relation to each other in the MTS, by attachment to an LM fixation element. Preferably, the LM fixation element maintains the LMs at their respective circumferential positions, for instance, it may maintain the distal terminal ends of the LMs in an annular ring. The proximal LM fixation element may be a disc or annulus disposed at an end of the MTS. It is preferably rigid.

The distal ends of the LMs are maintained in fixed relation to each other in the MTS. The distal ends of the LMs, more preferably the distal terminal ends of the LMs, may be connected to a distal LM fixation element. Preferably, the distal LM fixation element maintains the LMs at their respective circumferential positions, for instance, it may maintain the distal terminal ends of the LMs in an annular ring. The distal LM fixation element may be, for instance, a disc or annulus disposed at the distal end of the MTS. It is preferably rigid.

Similarly, the proximal ends of the LMs, more preferably the proximal terminal ends of the LMs, may be maintained in fixed relation to each other in the MTS. The proximal ends of the LMs may be connected to a proximal LM fixation element. Preferably, the proximal LM fixation element maintains the LMs at their respective circumferential positions, for instance, it may maintain the proximal terminal ends of the LMs in an annular ring. The proximal LM fixation element may be a disc or annulus disposed at the proximal end of the MTS. It is preferably rigid.

The LMs are slidable relative to each other, to the extent that movement is restricted by said LM fixation element(s). It is appreciated distal terminal ends of each LM in the set are maintained in fixed relation to each other (by the distal LM fixation elements), and the proximal terminal ends of each LM in the set are maintained in fixed relation to each other (by the proximal LM fixation elements) and hence the LMs do not slide relative to each other at the proximal and distal terminal ends. The application of force—pushing and/or pulling—at the proximal end of the MTS is transmitted via the LMs along the LMSR to the LMBDP which in turn causes movement of the TBPP e.g. by pulling or pushing the aforementioned fixation element(s).

The number of LM in the set may be at least two, for instance, 2, 3, 4, 5, 6, 7, 8, 9, 10, 11, 12, 13, 13, 14, 15, 16, 17, 18, 19, 20, 22, 24, 26 or more. For omni-directional steering, it is preferred that at least 4, more preferably at least 6 or 8 LMs, even more preferably 18 to 22 are present in the set.

An LM has a length, thickness and width (see FIGS. 13A and 13B). A width is the distance across a plane section in longer direction. A plane section is typically a transverse cross-section perpendicular to the longitudinal central (L-L') axis of an LM. A thickness is the distance across the plane section in shorter direction. The longer and shorter directions are perpendicular to each other. Where one of the sides of the plane section is straight, one direction is parallel to said straight edge. The width of the LM may be constant in the longitudinal direction. The thickness of the LM may be constant in the longitudinal direction. The thickness and width may be the same for instance, when the plane section is square or round. The length of the LM refers to the longitudinal length.

Dimensions of an LM may depend on the diameter and length of the eventual steerable tool, and on the number of LMs utilised. As a general guidance, an LM may have a thickness in one direction of 40 µm, 50 µm, 60 µm, 80 µm, 100 µm, 200 µm, 200 µm, 400 µm or 500 µm, or a value in the range between any two of the aforementioned values. An LM may have a width of 80 µm, 100 µm, 120 µm, 140 µm, 160 µm, 180 µm, 200 µm, 300 µm, 400 µm, 500 µm, 600 µm, 700 µm, 800 µm, 900 µm, 1000 µm, 1100 µm, 1200 µm, 1300 µm, 1400 µm, or 1500 µm or a value in the range between any two of the aforementioned values. The skilled person would understand how to select a suitable thickness and width according to the diameter of the MTS. For a 10 mm diameter MTS, the preferred thickness is 280 µm to 320 µm, preferably about 300 µm, and the preferred width is 480 µm to 520 µm, preferably about width 500 µm in the LMBDP, LMSR and optionally LMBPP. The length of the MTS will depend on the length of the steerable tool and its application. The above preferred dimensions apply to MTS of 37-40 cm in length.

The LMs may be made from any suitable material having the appropriate tensile and compression properties and can be deduced by the person skilled in the art. Examples include stainless steel or nitinol, beta titanium, spring steel, or polymer.

The LM may be made from a single strand of a material e.g. a single strip of stainless steel. Alternatively, it may be made from multiple strands of material tandemly connected.

The LMs are longitudinally arranged around the fictive tube. The LMs may be distributed evenly around the fictive tube e.g. the distance between adjacent LMs may be essentially the same. The LMs may distributed symmetrically around the fictive tube e.g. there may be a plane of symmetry about a longitudinal-cross section of the fictive tube. The LMs may be distributed unevenly around the fictive tube e.g. the distance between at least two pairs of adjacent LMs may be different.

The LM is preferably disposed essentially along the length of the MTS, and of the steerable tool. It spans the TBDP and extends into the TSR, and the TBPP where present.

The LMs are preferably arranged such that their longitudinal axes are mutually parallel. The LMs are preferably arranged such that their longitudinal axes are parallel to a longitudinal axis (A-A') of the fictive tube. The LMs are preferably arranged such that their longitudinal axes are parallel to a longitudinal axis of the longitudinal steerable tool.

The MTS is provided with a set of LM guides configured to support and maintain the arrangement of LMs around the fictive tube. There may be 2 to 30, more preferably 3 to 20 LM guides in the set. In particular, the set of LM guides maintain the set of LMs at a constant circumferential position on the fictive tube. In particular, the set of LM guides may axially rotationally constrain the LMs of the set, in particular at the TBDP and TBPP where present.

One or more LM guides of the set ("articulated LM guides" herein) may be articulated with respect to each other, particularly mutually pivoted, thereby supporting bending of the LMs, akin to a wrist joint. Articulated LM guides may be disposed in the TBDP and in the TBPP where present, corresponding to the BDP and the BPP of the steerable tool. In a MTS of 30 to 40 cm in length and a diameter of 6 mm to 8 mm, the TBDP may contain between 5 and 10 articulated LM guides.

One or more LM guides of the set ("fixed LM guides" herein) may be rotationally fixed with respect to each other, thereby maintaining a fixed (non-bending) path of the LM. Fixed LM guides may be disposed in the TSR, corresponding to the SR of the steerable tool, giving rise to an essentially rigid or semi-rigid TSR. In an MTS of 30 to 40 cm in length and a diameter of 6 mm to 8 mm, the TSR may contain between 13 and 17 fixed LM guides.

As mentioned above, the TSR may become rigid or semi-rigid when co-operating with a rigid or semi-rigid exotube or outer tube. In other words, the TSR may be flexible. Rigidly may be applied by inserting the TSR into a rigid or semi-rigid tube, or by clamping a rigid or semi-rigid tube around the TSR. Hence, articulated LM guides may be disposed in the TSR, corresponding to the SR of the steerable tool.

An LM guide comprises a body having a distal side and a proximal side, and an outside edge or surface connecting the distal and proximal sides. The outside edge can be rounded, straight or have any profile.

Figure 20:
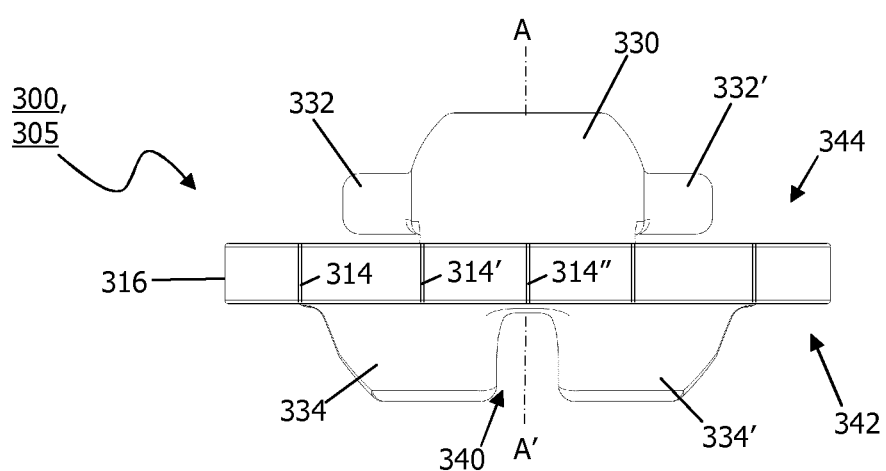
FIG. 20 is a side view of a LM guide that is an articulated LM guide.

For an articulated LM guide, the body is preferable substantially disc-shaped as shown, for instance, in FIG. 20. The body may be disposed with one component of a pair of components of a pivot joint on the proximal side of the body and the other component of the pair on the distal side of the body. Such a pivot joint may be a ball and socket joint. Adjacent articulated LM guides hence form a joint for mutual pivoting. As a general guidance for instruments such as surgical instruments, a disc-shaped body may have a diameter of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. The outside edge of the body may have a thickness of 0.1 cm, 0.15 cm, 0.2 cm, 0.25 cm, or a value between any two of the aforementioned values, preferably between 0.1 cm and 0.2 cm.

For a fixed LM guide, the body is preferable substantially cylindrically shaped, the ends of the cylinder being the distal and proximal sides. As a general guidance for instruments such as surgical instruments, a cylindrical body may have a diameter of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. The diameter of the articulated LM guide and the fixed LM guide may be the same. The thickness of the outside edge of the body may be, for instance, 0.5 cm, 0.6 cm, 0.8 cm, 1 cm, 2 cm, 3 cm or more, or a value between any two of the aforementioned values, preferably between 1 cm and 3 cm. While it is preferred that a plurality of tandemly arranged, fixed LM guides is present, it is within the scope of the invention that a single, long fixed LM guide is disposed in the TSR, corresponding to the SR of the steerable tool. A single fixed LM guide may be up to 10 cm, 20 cm, 30 cm, 40 cm or 50 cm in length, or a value between any two of the aforementioned values, or a value between any two of the aforementioned values, A single fixed LM guide can be formed by known processes such as extrusion. By tandemly arranged it is meant that the fixed LM guides are arranged end to end. Specifically, the proximal side of one fixed LM guide is in contact with the distal side of an adjacent fixed LM guide within the tandem arrangement. It is within the scope of the invention that there is one fixed LM guide.

Preferably, the body of the LM guide, either articulated or fixed is a one-piece element, e.g. is formed by moulding, extrusion or machining as one piece, avoiding the assembly of a plurality of elements.

The body is provided with a set of channels. The number of channels in the set may be at least two, for instance, 2, 3, 4, 5, 6, 7, 8, 9, 10, 11, 12, 13, 13, 14, 15, 16, 17, 18, 19, or 20, or more. For omni-directional steering, it is preferred that at least 4, more preferably at least 6 or 8 channels are present in the set. The number of channel in the set of channels may be equal to the number of LMs in the set of LMs. A channel comprises a void space in the body of the LM guide. A channel passes from the distal side to the proximal side of the LM guide body. A channel connects the distal side to the proximal side of the LM guide body. A channel preferably has a central axis from the distal side to the proximal side of the body that is parallel to the central axis (A-A') of the LM guide. Each and every channel of the set may be separate; in other words, the channels may not be interconnected. A channel can accommodate one, two, or more LMs, preferably only one LM. A channel is configured to constrain the LM, in particular to prevent radial movement with respect to the central axis of the body. A channel may be configured to constrain the LM, to prevent axial rotation, i.e. about the LM longitudinal (B-B') axis. A channel is dimensioned to facilitate longitudinal slidable movement of the LM therethrough. The channels may be arranged around a fictive tube. The channels contact the fictive tube. The fictive tube is preferably cylindrical. Said fictive tube corresponds with the fictive tube of the MTS. The channels of the set are mutually spatially separated. A channel may contain a transverse profile that complements the profile of the LM to be accommodated. A transverse profile is perpendicular to the central axis of the channel. For instance, where the LM has a rectangular profile, the channel may contain a rectangular profile. It is appreciated that the channel profile need not precisely mirror the profile of the LM, for instance a race-track LM profile may be constrained by a rectangular channel.

A channel has a width, height and thickness (see FIGS. 12A and 12B). The thickness is equal to the thickness of the body. The height of the channel is the smallest distance from a base wall of the channel to a top wall of the channel measured in a straight line. The width of the channel is the smallest distance between opposing channel side walls measured in a straight line. The base wall, top wall and side walls are preferably planar.

A channel is connected to the outside edge of the body of the LM guide by a slot, as shown for instance in FIGS. 7, 8, 9, and 12A. The slot passes from the proximal side to the distal side of the body. A slot preferably has a central axis from the distal side to the proximal side of the body that is parallel to the central axis (A-A') of the LM guide. The slot is preferably straight in the direction from the proximal side to the distal side of the body. The slot is preferably continuous from the proximal side to the distal side of the body. The slot is dimensioned to retain the LM in the channel; the slot is not so large that the LM can exit the channel through the slot. The slot has a width, height and thickness as shown in FIGS. 12A and 12B. The thickness is equal to the thickness of the LM guide body. The height of the slot is the smallest distance from the base of the slot—where it connects with the channel—to the outside edge of the body measured along a straight line. The width of the slot is the smallest distance between the slot side walls measured in a straight line. The slot side walls are preferably planar. Where are several distances measured at different points provide different results, the distance is the shortest distance. The width of the slot is such that the LM retaining function of the channel is maintained. The width of the slot is less than the width of the channel. The width of the slot is preferably less than 2%, 5%, 10%, 20%, 30%, 40%, 50%, 60%, 70%, 80%, 90% of the width of the channel and at least 0.5% of the width of the channel, or lies in a range between any two of the aforementioned values compared with the width of the channel.

The slot provides access to the channel from the outside edge of the LM guide. In particular the slot allows access to the LM, allowing it to be pulled into position during assembly of the MTS. More in particular, the slot allows the LM to be inserted through channels aligned in an array of empty tandemly-arranged LM guides by pulling the LM therethrough. For assembly of the steerable tool, the pushability of the LMs is a factor for longer instruments e.g. of 30 cm or more in length. An LM is generally thin and narrow to maximise the number available in the MTS for omnidirectional steering. The ability for advancement through a set of pre-arranged LM guides during manufacture is diminished owing to a buckling effect at the threading end. Friction within the channels increases the force required to advance each LM by pushing. In practice, assembly is performed by manually threading each LM guide onto the set of LMs, which is time consuming, unwieldy for longer MTSs, and increases manufacturing costs. The slot presently described allows the LM guides of the MTS to be pre-assembled, and, with the slots of tandemly arranged LMs guides aligned to form an effective groove accessible from the exterior of the MTS, it facilitates the application of an external pulling force in the direction of the groove (see FIG. 9A). The external pulling force can be applied by an external tool, configured for insertion into the slot and for dismountable attachment to the LM. The LM may be modified for attachment to such a tool; for instance it may be disposed with a hole at one end to provide a point of engagement with a hooked external tool. Equally, the LM may be unmodified, the external tool being provided with a gripper.

According one aspect of the invention, the LM is disposed with a tail as shown, for instance, in FIG. 14A. The tail is preferably straight. A central longitudinal axis of the tail is preferably co-axial with a central longitudinal axis of the adjoining LM. The tail has a tail trailing end at one end attached to the LM, and at the other end, a tail leading end. The tail is configured for passage through the slot of the LM guide. Specifically, at least the trailing end of the slot is configured for passage through the slot. By passage through the slot, it is meant that the wider side (width) of the tail is configured to be pushed into the slot.

A tail has a width, length and thickness (see FIGS. 14A and 14B). A width is the distance across the plane section in longer direction. A plane section is typically a transverse cross-section perpendicular to the longitudinal central axis of a tail. A thickness is the distance across the plane section in shorter direction. The longer and shorter directions are perpendicular to each other. Where one of the sides of the plane section is straight, one direction may be parallel to said straight edge. The thickness and width may be the same for instance, when the plane section is square or round. The length of the tail refers to the longitudinal length.

The tail is may be provided at one or both ends of the LM, more preferably at one end. The tail is preferably at the proximal end of the LM. The tail is typically a continuation of the LM at one or both ends. The thickness of the tail may be the same as the thickness of the LM. The tail has a width that is less than the width of the LM. The width of the tail is dimensioned such that the tail width enters the slot of the LM guide. In other words, the widest surface of the tail is configured to be pushed into the slot of the LM guide. Hence it can be introduced into the channel by pushing into the slot from the exterior of the MTS.

The tail width may be equal to or less than 110% of the LM guide slot width. Although the tail width can be slightly greater than the slot width (by 10%), compliance of the tail and of the LM guide still allows passage through the effective groove. The tail width may be less than the width of the slot of the LM guide, for instance it may be equal to or less than 70%, 80%, or 90% of the LM guide slot width. The tail, being able to enter the slot can be pushed or pulled through the effective groove formed by the tandemly arranged LM guides, and hence through the aligned channels during assembly of the MTS. The tail may replace the aforementioned external tool. The tail does not require threading through the channel from the proximal or distal side, thereby reducing the need for a skilled assembly. The tail may be incorporated into the MTS, preferably in the TBPP.

Preferably the LM with tail are made from a continuous sheet of material, for instance by laser cutting. Alternatively, the LM with tail may be made formed from a polymeric material in a moulding process.

The tail leading end may be provided with an end stop (see FIGS. 15A, 16, 17 and 18). The end stop acts as a stop bar, preventing the tail leading end from entering the slot. The end stop is configured to prevent the tail leading end from entering the slot. The end stop is configured to maintain the tail leading end outside the slot from the outside edge of the LM guide. Typically, the end stop contacts the outside edge of the LM guide, and limits entry of the tail leading end into the slot. The end stop is configured to attach to the LM fixation element (see FIGS. 16 to 18), together with end stops from other LMs, for instance by attachment to a rigid annular ring. Because the end stop is wider than the tail, it serves to anchor the end of the LM to the LM fixation element. In particular the end stops provide a greater surface area for attachment to the LM fixation element; the adhesive fixes the end stops into position onto the LM fixation element. The construction provides effective resistance to pushing and pulling forces that would otherwise cause the linear LM to slide away from the fixation element.

The end stop may further be configured for gripping manually, or by a mechanical gripper or for magnetic attachment to pull the LM through the effective groove during assembly.

The end stop has a width, length and thickness (see FIGS. 15A and 15B). A width is the largest distance across a plane section in a direction perpendicular to the central longitudinal axis of the tail. A plane section is typically a transverse cross-section perpendicular to the longitudinal central axis of the tail extending into the end stop. A thickness is the distance across the plane section in the shortest direction. The length of the end stop refers to the length measured co-axial to the central longitudinal axis of the tail. The end stop width is greater than the slot width. Preferably, the end stop width is greater than the tail width. The end stop may have the same width as the LM width. The end stop may have a greater width compared with that of the LM, for instance, it may be 10%, 20% or 30% wider than that of the LM. Where the end stop width is greater than the LM width, entry of the end stop into the channel is also prevented.

The end stop may have any geometric shape that prevents entry into the LM guide slot. For instance, it may have a planar form, for instance substantially square, rectangular, circular, oval, triangular or other polygonal outer profile. To aid attachment to the LM fixation element by adhesive, it may contain one or more notches or holes. Alternatively, the end stop may comprise a linear (one dimensional) shape, for instance an undulating pattern characterised by a repeating crests and troughs, which may be, for example, zig-zag, or wavy, or an array of interconnected "Y"s connected by the Y-arms, thus "YYY" (see FIG. 22). Typically the undulating pattern is disposed perpendicular to the longitudinal axis of the tail. Typically the trough or the crest is attached to the tail.

Figure 17:
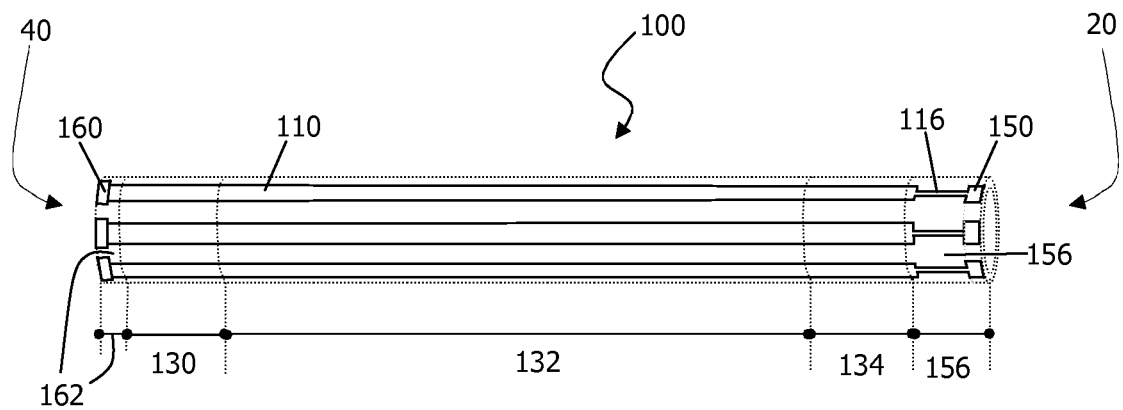
FIG. 17 is a schematic view of a set of LMs provided in a MTS each LM disposed at the proximal end with a tail, and end stop and disposed at the distal end with an anchoring tab.
Figure 19:
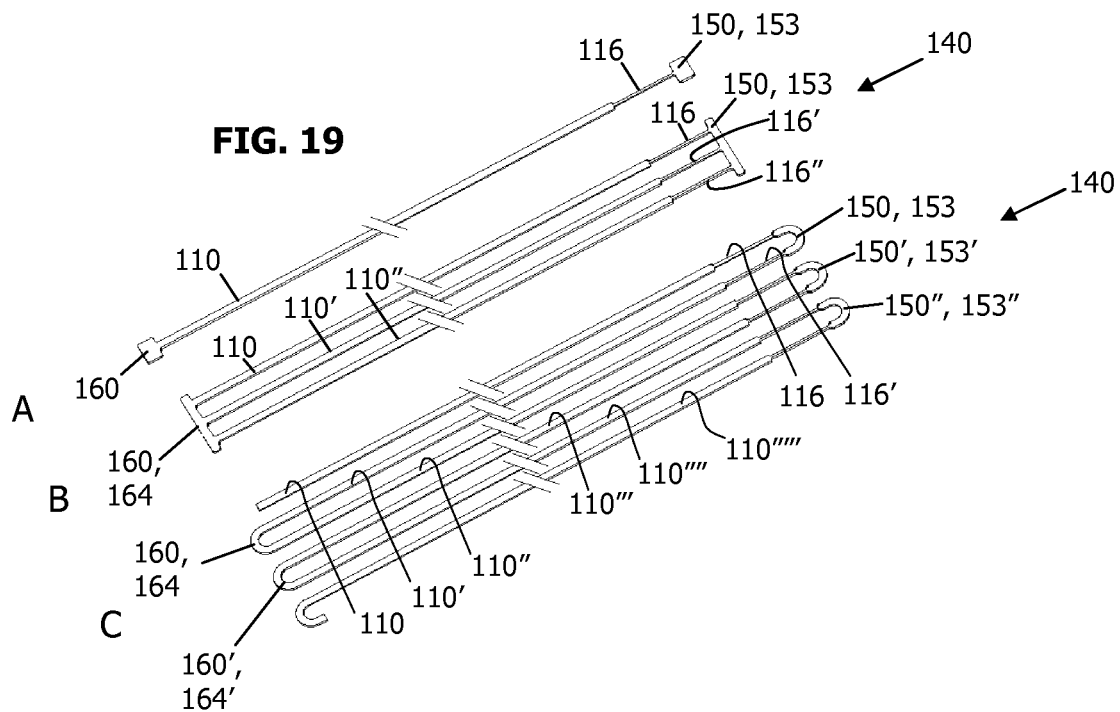
FIG. 19A is an isometric view of a single LM provided with a tail, end stop, and anchoring tab.
FIG. 19B is an isometric view of an LM assembly.
FIG. 19C is an isometric view of an alternative LM assembly.

The non-tailed end of the LM, typically the distal end, may be provided with an anchoring tab as shown, for instance, in FIGS. 17 and 19A. The anchoring tab acts as a stop bar, preventing the LM from advancing through the slot or channel. The anchoring tab is to configured to limit entry into the channel of the LM guide. The anchoring tab is configured to limit entry of the attached LM through the channel of the LM guide. The anchoring tab is configured to maintain the LM outside the channel from the distal side of the LM guide. Typically, the anchoring tab contacts the distal side of the LM guide, and limits entry of the LM into the channel.

The anchoring tab has a width, length and thickness. A width is the largest distance across a plane section in a direction perpendicular to the central longitudinal axis of the tail. A plane section is typically a transverse cross-section perpendicular to the longitudinal central axis of the LM extending into the anchoring tab. A thickness is the distance across the plane section in the shortest direction. The length of the anchoring tab refers to the length measured co-axial to the central longitudinal axis of the LM. The anchoring tab width is greater than the slot width. The anchoring tab may have a greater width compared with that of the LM, for instance, it may be 10%, 20% or 30% wider than that of the LM; entry of the end stop into the channel is also prevented by the greater width.

The anchoring tab is configured for attachment to the LM fixation element (see FIG. 17), specifically to the distal LM fixation element. Typically, the anchoring tabs from other LMs, are attached to the LM fixation element thereby forming a rigid annular ring. Because the anchoring tab is wider than the LM, it anchors the end of the LM to the LM fixation element. In particular when the anchoring tabs and LM fixation element are anchoring tab is better fixed into position onto the LM fixation element. The construction provides effective resistance to pushing and pulling forces that would otherwise cause the LM to pull away from the fixation element. Alternatively, adjacent anchoring tabs in the MTS may combine to form a common anchoring tab, that serves as a single annular LM fixation element (see FIGS. 18 and 19B), which may or may not be circumferentially intact. Where the LMs are provided as a rollable LM assembly as described below, such as in FIG. 19B, the single annular LM fixation element formed from a common anchoring tab would not be circumferentially intact.

The anchoring tab may have any geometric shape that prevents entry into the LM guide slot or channel. For instance, it may have a planar form, for instance substantially square, rectangular, circular, oval, triangular or other polygonal outer profile. To aid attachment to the LM fixation element by overmolding, it may contain one or more notches or holes. Alternatively, the anchoring tab may comprise a linear (one dimensional) shape, for instance an undulating pattern characterised by a repeating crests and troughs, which may be, for example, zig-zag, or wavy. Typically the undulating pattern is disposed perpendicular to the longitudinal axis of the tail. Typically the trough or the crest is attached to the LM member.

One aspect of the invention provides an LM assembly, comprising two or more LMs arranged mutually parallel, wherein the leading ends of at least two tails are connected to a common end stop (see FIGS. 19B and 19C). The common end stop has the same functionality as an end stop insofar as it acts as a stop bar, preventing the tail leading end of each LM from entering the respective slots of the LM guide.

Preferably, the number of LMs in an LM assembly is equal to the number of LMs in the set i.e. the number that constitutes a MTS. The tail is preferably at the proximal end of each LM.

Preferably, the edges of the LMs are arranged mutually adjacent i.e. the edges of a pair of LM guides within the LM assembly are adjacent so as to have the possibility to form a sheet-like or planar structure. The distance between adjacent LMs may be equal to that between adjacent slots in the LM guide. Hence the LM assembly can be curved along its longitudinal axis and applied to vacant set of tandemly arranged LM guides, thereby inserting simultaneously, a plurality of LMs.

According to one variant, the free end of each and every tail is connected to a single common end stop (see FIG. 19B). The single common end stop may be attachable to the LM fixation element, preferably to the proximal LM fixation element. The common end stop may be formed from a continuous connecting strip (see FIG. 19B), or from individual anchoring tabs adjacently joined. The common end stop may comprise a linear shape, for instance an undulating pattern (see FIG. 22) characterised by a repeating crests and troughs, which may be, for example, zig-zag, wavy, or an array of interconnected "Y"s connected by the Y-arms, thus "YYY", and attached to the tail by the "Y" stem. Typically the undulating pattern is disposed perpendicular to the longitudinal axis of the tail. Typically the trough or the crest is attached to the LM member.

According to another variant, pairs of adjacent LMs are connected to a single common end stop by their tails (see FIG. 19C); in other words, each common end stop connects only two adjacent LMs. Pairs of adjacent common end stops may not be interconnected.

The non-tailed end of each and every LM in the LM assembly may be connected to a common anchoring tab (see FIG. 19B). The common anchoring has the same functionality as an end stop insofar as it acts as a stop bar, preventing each LM from advancing through the respective channels of the LM guide. The non-tailed end is preferably the distal end. The common anchoring tab forms an LM fixation element, preferably a distal LM fixation element. The common anchoring tab may be formed from a continuous connecting strip (see FIG. 19B), or from individual anchoring tabs adjacently joined (see FIG. 22). The common anchoring tab may comprise a linear shape, for instance an undulating pattern characterised by a repeating crests and troughs, which may be, for example, zig-zag, wavy, or an array of interconnected "Y"s connected by the Y-arms, thus "YYY". Typically the undulating pattern is disposed perpendicular to the longitudinal axis of the tail. Typically the trough or the crest is attached to the LM member.

According to another variant, the non-tailed ends of pairs of adjacent LMs in the LM assembly may be connected to a common anchoring tab (see FIG. 19C); in other words, each common anchoring tab connects only two adjacent LMs. Pairs of adjacent common anchoring tabs may not be interconnected.

Pairs of adjacent LMs may be connected to a common end stop by their tails, and the non-tailed ends of pairs of adjacent LMs may be connected to a common anchoring tab (see FIG. 19C), thereby forming a snaking chain of LMs connected by the end stops and anchoring tabs.

The LM assembly can be prepared from a sheet of material such as nitinol by techniques such as laser cutting, photochemical etching, deep pressing, conventional chipping techniques such as drilling or milling, high pressure water jet cutting systems or any suitable material-removing process. Preferably laser cutting is used to provide cut accuracy. The LM assembly allows the LMs and fixation components to be manufactured from a sheet of material in one convenient process, and further pre-aligns the LM in a parallel configuration.

Alternatively, the LM assembly, for instance, having a snaking structure (see FIG. 19C), may be formed from a strand of wire that is stamped so as to produce the LM, tail, single end stop and single anchoring tab. The stamped wire is subsequently bent at each single end stop and single anchoring tab so as to adopt the requisite snaking form.

One aspect provides an expandable sheet (see FIG. 21) provided with a pattern of cuts, defining a set of LMs arranged mutually parallel, defining a set of tails arranged mutually parallel and each attached their trailing ends to a separate LM, and defining a common end stop having an undulating form and attached to the leading ends of the tails. The expandable sheet may be planar. The common end stop is preferably expandable. In a preferred aspect, the common end stop comprises an undulating pattern characterised by a repeating crests and troughs, which may, for example, appear in the expanded state as a zig-zag, wavy, or an array of interconnected "Y"s connected by the Y-arms, thus "YYY", and attached to the tail by the "Y" stem. Typically the undulating pattern is disposed perpendicular to the longitudinal axis of the tail. Typically the trough or the crest is attached to the LM member. Expansion or stretching of the expandable sheet produces an LM assembly (see FIG. 22) having a set of LMs arranged each attached at one to a tail wherein the tails are each attached at their leading ends to a common end stop that comprises an undulating pattern.

The other (non-tailed) end of the expandable sheet may or may not be expandable. Where it is not expandable, the other (non-tailed) end of each LM may be attached to a common anchoring tab; the common anchoring tab may be non-expandable. Expansion of the sheet gives rise to a fan-shaped structure. Where the other (non-tailed) of the expandable sheet is expandable, the expansion of the expandable sheet may also give rise to the common anchoring tab attached to other end of each LM; the common anchoring tab may have an undulating pattern. Expansion of the sheet may give rise to an essentially rectangular form (square or oblong).

The sheet is typically expandable in a planar direction. The sheet is typically expandable in a direction essentially perpendicular to the longitudinal axis of the LM. The sheet is typically not expandable in a direction essentially parallel to the longitudinal axis of the LM. The expandable LM assembly reduces waste as cut-out sections between adjacent LM members is eliminated.

The expandable sheet has a non-expanded state and an expanded state. The expandable sheet is preferably stable in both states. The expandable planar sheet may be configured for expansion from the non-expanded state to the expanded state. Expansion of the expandable sheet may be non-returnable; by non-returnable, it is meant once expanded, the expandable sheet cannot return to the non-expanded state.

The expandable planar sheet may have a greater width (w) after planar expansion. The width is the maximum distance across the planar sheer in the direction of expansion. Typically, the width is the distance across the planar sheer in a direction essentially perpendicular to the longitudinal axis of an LM.

The LM assembly may be an LM assembly as defined herein.

The expandable sheet may be formed by any suitable technique for making cuts in a sheet. For instance, by means of different techniques such as laser cutting, photochemical etching, deep pressing, conventional chipping techniques such as drilling or milling, high pressure water jet cutting systems or any suitable material removing process available. These are convenient ways as the expandable sheet can be made in one process, thereby simultaneously preparing multiple LMs.

The expandable sheet may be made from any suitable material such as stainless steel, nitinol, or polymer. The material may be non-compliant in the direction of expansion.

The invention further provides a plurality of LM guides. The LM guides are preferably tandemly arranged such that the slots are aligned to form an effective groove. The effective groove is preferably straight. The effective groove is preferably parallel to the central axis of the LM guides. The effective groove allows access to the channels and a path for pulling the LM therethrough and/or allows passage of the tail and end stop.

The set of LM guides is tandemly arranged i.e. distal side of one LM guide faces the proximal side of an adjacent LM guide. An example of tandemly-arranged articulated LM guides is shown in FIGS. 1, 3 to 5 and 9. The articulated LM guides in the set of LM guides are mutually (pairwise) articulated. Preferably, the articulated LM guides are in mutual (pairwise) contact. Preferably, an articulated LM guide contacts an adjacent LM guide using a pivot joint, such as a ball-and-socket type joint. The pivot joint allows pivoting of an articulated LM guide with respect to an adjacent articulated LM guide. The pivot joint may allow two degrees of freedom of movement with respect to an adjacent articulated LM guide i.e. roll and pitch. The pivot joint may or may not also allow relative rotation of adjacent articulated LM guides (i.e. yawing or axial rotation between adjacent articulated LM guides). Prevention of yawing can be achieved for instance, using a rotation limiter that might be a protrusion fixed on the body of one articulated LM guide that is received by a recess fixed on the body of an adjacent articulated LM guide (as shown, for instance, in FIG. 17); coupling prevents axial rotation of one LM guide relative to the adjacent LM guide.

The one or more fixed LM guides of the set of LM guides are mutually (pairwise) in fixed relation. They are preferably in fixed rotational relation. They are preferably in fixed distance relation. Preferably, the one or more fixed LM guides are in mutual (pairwise) contact.

The LM guides of the set are tandemly arranged such the circularly-arranged channels are in alignment, and each can receive one (or optionally two or more) LMs.

Preferably, the articulated LM guide is substantially disc-shaped, is provided with 10-20 channels each configured to accommodate only one LM, each channel containing a rectangular transverse profile and connected to the outside edge by the slot, the long side of the rectangle oriented to face a central axis of the LM guide, the channels being arranged around a fictive tube. The channel width is preferably 0.55 to 0.65 mm. The slot width is preferably 0.2 to 0.3 mm. The articulated LM guide preferably has an outer diameter of 0.9 to 1.1 cm, and a body thickness of 0.9 to 1.75 mm. The fictive tube in the TBDP preferably has an outer diameter of 0.75 to 0.85 cm. Preferably, the fixed LM guide is substantially cylindrically-shaped, is provided with 10-20 channels each configured to accommodate only one LM, each channel containing a rectangular transverse profile and connected to the outside edge by the slot, the long side of the rectangle oriented to face a central axis of the LM guide, the channels being arranged around a fictive tube. The channel width is preferably 0.55 to 0.65 mm. The slot width is preferably 0.2 to 0.3 mm. The fixed LM guide preferably has an outer diameter of 0.9 to 1.75 cm, and a body thickness of 1.5 to 2.5 cm. The fictive tube in the TSR preferably has an outer diameter of 0.75 to 0.85 cm.

Each channel is configured to constrain the LM to reduce or prevent axial rotation, and to maintain its radial position with respect to a central LM guide axis (A-A').

The MTS may be provided with an end effector, and configured such that the end effector is rotationally fixed in relation to the LMBDP, and the end effector is rotatable when the LMBDP is in a bent position, by a complementary rotation of the LMBPP. Hence, the steerable tool may be configured such that the end effector is rotationally fixed in relation to the BDP and the end effector is rotatable when the BDP is in a bent position, by a complementary rotation of the BPP. The rotationally fixed effector end may be realised by a permanent attachment to the tip of the LMBDP or BDP, for instance be welding or adhesive. Alternatively, the rotationally fixed end effector may be realised by a lockable revolute attachment to the tip of the LMBDP or BDP, in which the end effector is rotationally fixed in relation when the end effector is locked in position.

Also provided is a method for assembly of a mechanical transmission system, MTS (100), for a steerable tool (500), which MTS (100) has a proximal end (20), a distal end (40), a transmission shaft region, TSR (132), and transmission bendable distal part (130, TBDP) adjacent to the TSR (132) that moves omnidirectionally responsive to actuation of the MTS (100) at the proximal end (20), comprising the steps:
  providing an LM assembly as described herein,
  providing a set of LM guides as described herein each with a set of channels and slots, which LM guides are arranged such that the respective slots form effective longitudinal grooves,
  rolling the LM assembly to form a tube,
  inserting the tails of the LMs into the respective slots of the end-most LM guide, the common end stop being maintained outside the slots, and
  advancing the LM assembly in a longitudinal direction, thereby threading the set LMs into the set channels.

The common stop is advanced outside the slots, and reaches the end of the MTS intact, where it may be attached to the LM fixation element, preferably to the proximal fixation element.

Reference is made in the description below to the drawings which exemplify particular embodiments of the invention; they are not at all intended to be limiting. It will be understood that the skilled person may adapt the device and substitute components and features according to the common practices of the skilled artisan.

FIG. 1 is an isometric view of a partial assembly process of an MTS 100 containing a set of tandemly arranged LM guides 300 of the invention aligned such that the slots form an effective groove. Three LMs 110, 110', 110" are each provided in a separate channel. The LM can be accessed via the slot 314. The LMs can be advancing by inserting a tool into the slot that connects with the LM, and pulling along the effective groove. An LM 110 can be inserted into the entire length of the MTS by a single motion. FIG. 1A shows a detail of two LMs 110 and 110' each fully housed in a channel 310 accessed by a slot 314.

FIG. 2 is an isometric view of a steerable tool 500 incorporating an MTS of the invention. The steerable tool 500 has a proximal 20 and distal 40 end. The distal end 40 is provided with an end effector 540 that is a gripper, while the proximal end 20 is provided with a handle 550 to steer the tube and to control the gripper. Also indicated are the bendable distal part (BDP) 530, the shaft region (SR) 532 and the bendable proximal part (BPP) 534.

FIG. 3 depicts an outer view of an MTS 100 containing LM guides 300 of the invention, having a proximal 20 and distal end 40, and transmission bendable distal part (TBDP) 130, a transmission shaft region (TSR) 132. The transmission shaft region (TSR) 132 is disposed with a plurality of fixed LM guides 350, 350', 350". The TBDP 130 is disposed with a plurality of articulated LM guides 305, 305', 305", 305a, 305a', 305a". Each LM guide is provided with a slot 314 providing access into the channel (not shown). The tandemly arranged slots 314 form an effective groove.

Figure 4:
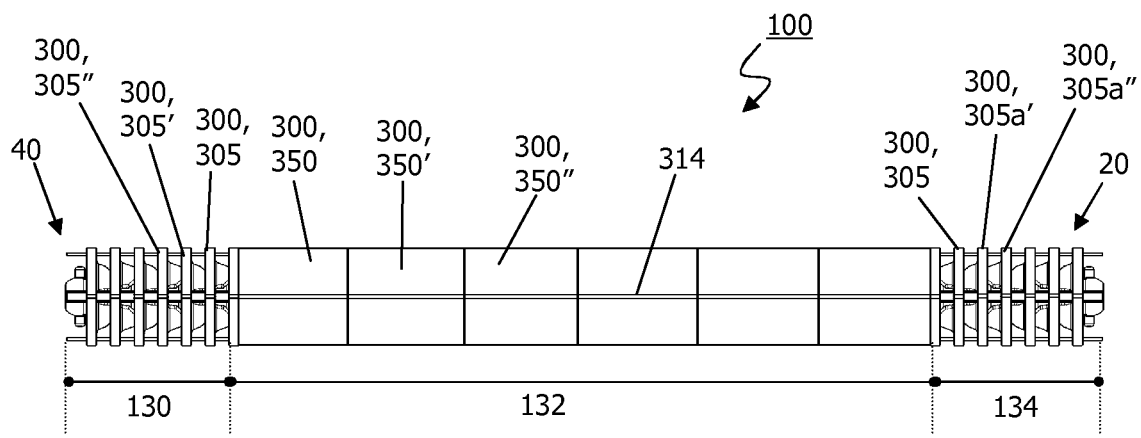
FIG. 4 depicts an outer view of an MTS containing longitudinal members (LM) guides of the invention as shown in FIG. 3 with the addition of a transmission bendable proximal part (TBPP).

FIG. 4 depicts an outer view of an MTS 100 containing LM guides 300 of the invention, as shown in FIG. 2, with the addition of a transmission bendable proximal part (TBPP) 134. The TBDP 130 and TBPP 134 are disposed with a plurality of articulated LM guides 305, 305', 305", 305a, 305a', 305a".

Figure 5:
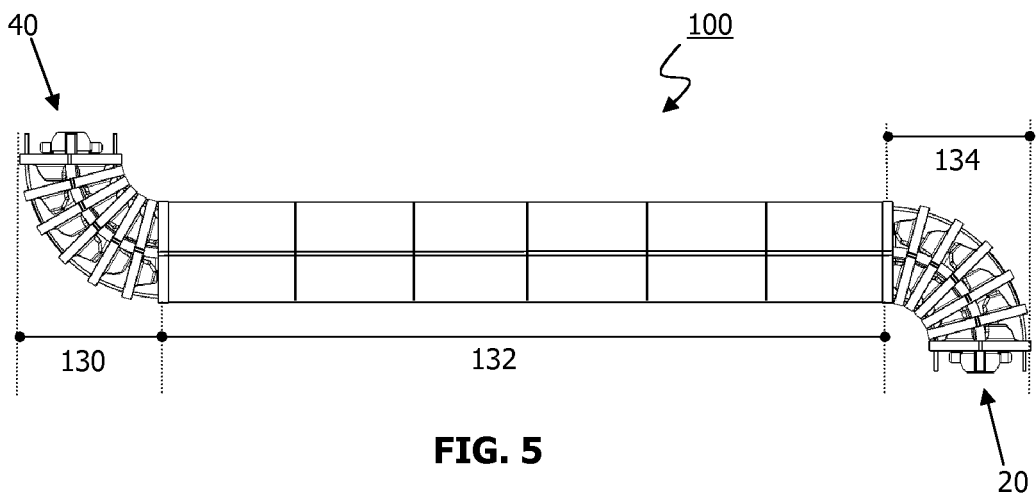
FIG. 5 depicts the MTS of FIG. 3, showing actuation of the transmission bendable proximal part (TBPP) and responsive bending of the transmission bendable distal part (TBDP).

FIG. 5 depicts the MTS 100 of FIG. 3, in which TBPP 134 has been actuated by bending, the movement transmitted to the TBDP 130 along the TSR 132 by the MTS, which TBDP 130 bends responsively.

Figure 6:
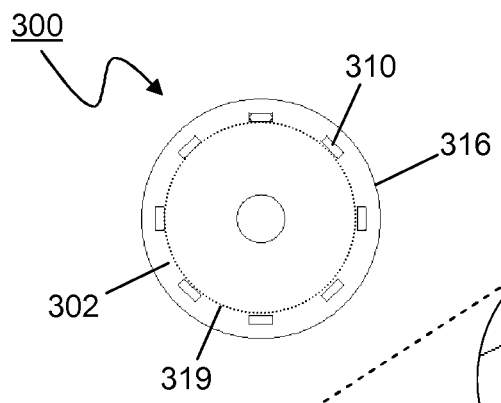
FIG. 6 is a plan view of an LM guide shown with set of channels without slots arranged around a fictive tube.

FIG. 6 is a plan view of an LM guide 300 shown without slots to emphasise the set of channels 310 arranged around a fictive tube 319, each for retaining an LM 110.

Figure 7:
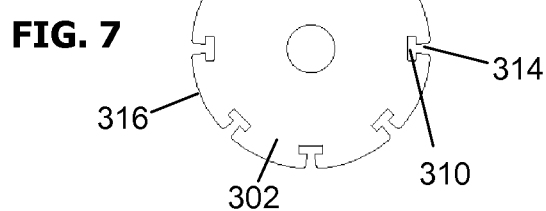
FIG. 7 is a plan view of an LM guide disposed with a set of channels each with a connecting slot arranged around a fictive tube.
Figure 7A:
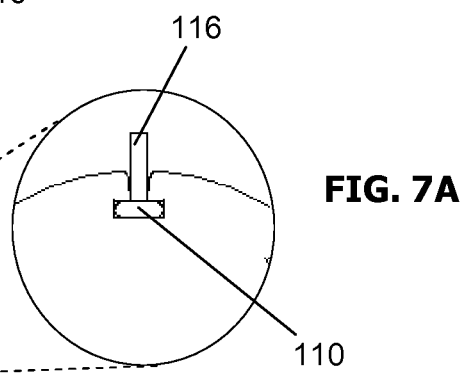
FIG. 7A is a detail of a channel of FIG. 7, with a LM present therein and a tail passing through a slot.

FIG. 7 is a plan view of an LM guide 300 of the invention disposed with a set of rectangular-profiled channels 310 for arranged around a fictive tube 319, each connected to the outside edge of the 316 of the LM guide 300 via a slot 314. Also shown is a LM 110 present in a channel (FIG. 7A) and a tail 116 passing through a slot.

Figure 8:
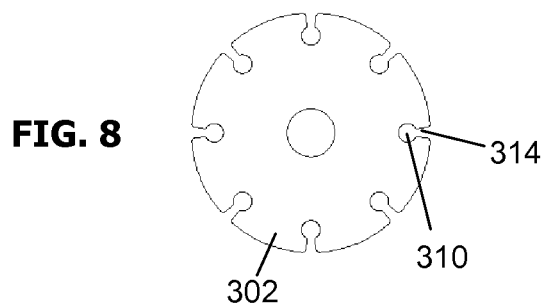
FIG. 8 is a plan view of an LM guide disposed with a set of circular-profiled channels each connected to the outside edge of the LM guide via a slot.

FIG. 8 is a plan view of an LM guide 300 of the invention disposed with a set of circular-profiled channels 310 for arranged around a fictive tube 319, each connected to the outside edge 316 of the LM guide 300 via a slot 314.

FIG. 9 is an isometric view of a partial assembly process of an MTS 100 containing a set of tandemly arranged LM guides 300 of the invention aligned such that the slots form an effective groove. Three LMs 110, 110', 110" are introduced by inserting the tails 116 thereof into the slot 314 and advancing it longitudinally. The end stop 150 prevents the leading edge 116b of the tail 116 from entering the slot 314. The end stops 150 may be later attached to an LM fixation element, for instance by attachment to a rigid annular ring (see FIGS. 17 and 18). The LMs each are advanced into the channels of distal 40 most LM guide, and by advancing further the tail 116, can be inserted into the entire MTS by a single motion. FIG. 9A shows a detail of an LM 110 fully housed in a channel, and of an LM 110' being guided into a channel 310 by the tail 116, which tail passes through a slot 314.

FIG. 10 is an isometric view of an LM 110 provided at one end with a tail 116, having a trailing end 116a attached to the LM 110, and a leading end 116b attached to an end stop 150.

The tail 116 is bent upwards for passing through the slot to position the end stop outside the slot and channel, and optionally for pulling along the effective groove formed by an alignment of slots in the MTS.

FIG. 11 is an isometric view of a LM 110 provided at one end with a tail 116, wherein the tail 116 is coaxial with the LM.

FIG. 12A is a plan view of a part of an LM guide 300 of the invention showing a channel 310 and slot 314 in detail together with dimensional indications that are the channel width 320, channel height 322, slot width 326 and slot height 314.

FIG. 12B is a side view of a part of an LM guide 300 of the invention showing a channel 310 and slot 314 in detail together with dimensional indications that are the channel width 320, slot width 326 and LM body thickness 328 which is equal to the channel thickness and slot thickness.

FIG. 13A is a plan view of a LM 110, together with dimensional indications that are the LM length 122 and LM width 124. A longitudinal axis (L-L') of the LM is also indicated.

FIG. 13B is a plane section of a LM at point B in FIG. 13A together with a dimensional indications that are the LM thickness 126 and LM width 124.

FIG. 14A is a plan view of a LM 110 disposed with a tail 116, together with dimensional indications that are the tail length 127 and tail width 128. The tail 150 has a trailing end 116a attached to the LM 110, and a free leading end 116b.

FIG. 14B is a plane section of a tail at point C in FIG. 14A together with a dimensional indications that are the tail thickness 129 and tail width 128.

FIG. 15A is a plan view of a LM 110 disposed with a tail 116 the end of which is provided with a rectangular end stop 150. The end stop length 151 is indicated. The leading end 116b of the tail 116 is attached to the end stop 150.

FIG. 15B is a plane section of a end stop at point D in FIG. 15A together with a dimensional indications that are the end stop thickness 152 and end stop width 154.

Figure 16:
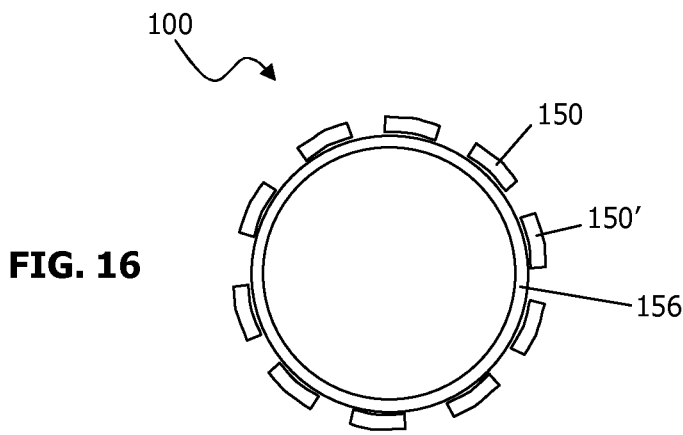
FIG. 16 shows a transverse plane section of an LM fixation element to which stop members are rigidly attached.

FIG. 16 is a transverse plane section of an LM fixation element 156 that is a rigid annular ring to which stop members 150, 150' of a set of LMs are rigidly attached.

FIG. 17 is a schematic view of a set of LMs 110 provided in a MTS 100 having a proximal 20 and distal end 40, and transmission bendable distal part (TBDP) 130, a transmission shaft region (TSR) 132. Each LM 110 is disposed at the proximal 20 end with a tail 116, and the leading end of the tail is attached to an end stop 150. Each LM 110 is disposed at the distal 20 end with an anchoring tab 160. The proximal 20 terminal end of the LM 110 is attached to a proximal LM fixation element 156; to strengthen the attachment, the tail 116 and the end stop 150 are also attached to the proximal LM fixation element 158. The end stop 150, being wider than the tail 116 provides an anchoring effect. The distal 40 terminal end of the LM 110 is attached to a distal LM fixation element 162; to strengthen the attachment, the anchoring tab 160 is also attached to the distal LM fixation element 162. The anchoring tab 160, being wider than the LM provides an anchor.

Figure 18:
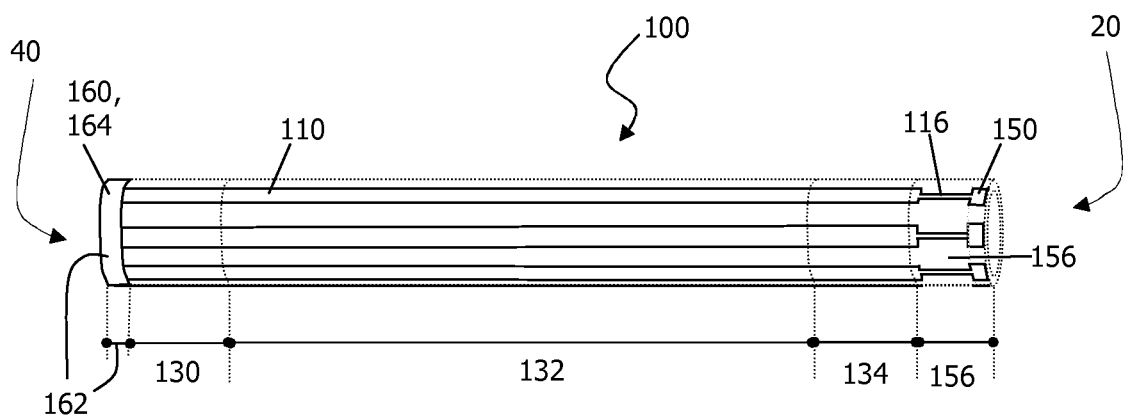
FIG. 18 is a schematic view of a set of LMs similar to that of FIG. 17, wherein each LM is attached to an anchoring tab that is a common anchoring tab at the distal end.

FIG. 18 is a schematic view of a set of LMs 110 similar to that of FIG. 17, wherein the distal 40 terminal end of each LM 110 is attached to an anchoring tab 160 that is a common anchoring tab 164 that also functions as a distal LM fixation element 162.

FIG. 19A is an isometric view of a single LM 110 disposed at one end with a tail 116 the leading end of which is provided with an end stop 150. The other end of the LM is provided with an anchoring tab 160.

FIG. 19B is an isometric view of an LM assembly 140 comprising three LMs 110, 110', 110" each disposed with a tail 116, 116', 116" the leading ends of which are disposed with an end stop 150 that is a single common end stop 153. The other end of each LM 110, 110', 110" is provided with an anchoring tab 160 that is a common anchoring tabe 164. The LMs are arranged such that their longitudinal axes are parallel and mutual edges are adjacent.

FIG. 19C is an isometric view of an alternative LM assembly 140 comprising multiple LMs 110, 110', 110", 110''', 110'''', 110''''', each disposed with a tail e.g. 116, 116' the leading ends of which are provided with an end stops 150, 150', 150" that are common end stops 153, 152', 153" each connecting an adjacent pair of LMs (e.g. common end stop 153 connecting LM 110 and 110'; end stop 153' connecting LM 110" and 110'''; end stop 150" connecting LM 110'''' and 110'''''). The other end of each LM 110, 110', 110", 110''', 110'''', 110''''' is provided with anchoring tabs 160, 160' that are common anchoring tabs 164, 164' connecting adjacent pairs of LMs (e.g. common anchoring tab 164 connecting LM 110' and 110"; common anchoring tab 164' connecting LM 110' and 110''''), so as to form a snaking chain of LMs. The common anchoring tabs 164, 164' may be later attached to an LM fixation element in the MTS. The LMs are arranged such that their longitudinal axes are parallel and mutual edges are adjacent.

FIG. 20 is a side view of a LM guide 300 that is an articulated LM guide 305 having a disc shaped body 302, and a distal side 344 and a proximal side 342 and disposed with a plurality of slots 314, 314', 314". A central axis (A-A') is indicated. The articulated LM guide 300 has a body 302 comprising at the distal side 344, one component of the pair of components that forms a pivot joint that is a dome protrusion 330, akin to the ball of a ball and socket joint. It further comprises at the proximal side 342, the other component of the pair of components that forms a pivot joint that is a reciprocating recess 340, akin to the socket of a ball and socket joint. Further indicated is a pair of rotation limiters (332, 332') fixedly connected to the dome protrusion 330, which are radial protrusions from said dome protrusion 330. These couple with a pair reciprocating slots 334, 334' fixedly connected to the receiving recess 340 of an adjacent articulated LM guide (not shown), to prevent mutual axial rotation of adjacent articulated LM guides.

Figure 21:
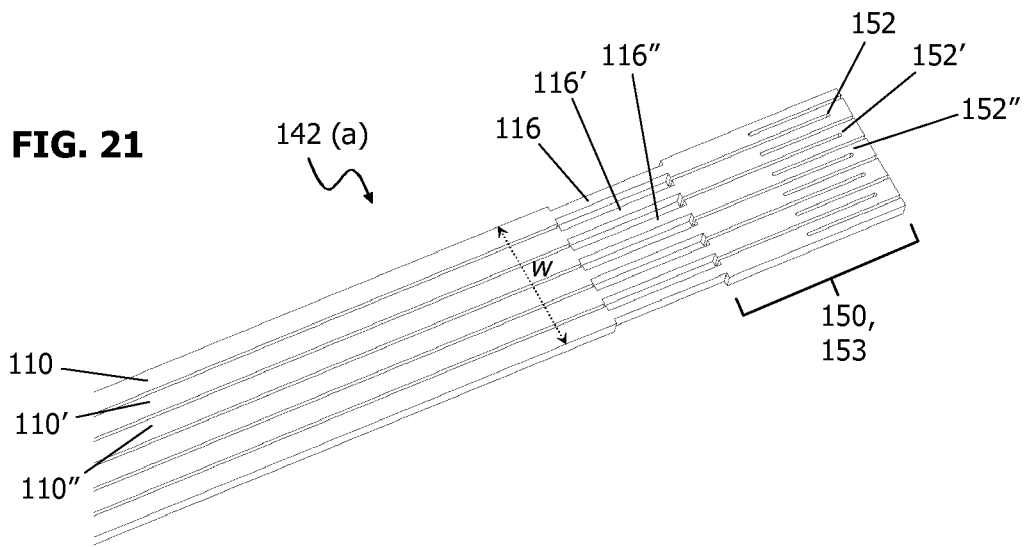
FIG. 21 is an isometric view of an expandable LM assembly

FIG. 21 is an isometric view of an expandable planar sheet 142(a), provided with a pattern of cuts defining a set of LMs 110, 110', 110" arranged mutually parallel, defining a set of tails 116, 116', 116" arranged mutually parallel and each attached by their trailing ends to an LM 110, 110', 110", and defining an end stop 150 that is a common end stop 153, having an undulating form and attached to the leading ends of the tails 116, 116', 116". Specifically, the common end stop is formed from an array of interconnected "Y"s 152, 152', 152" joined by the Y-arms, thus "YYY" in the expanded state. The planar sheer (142)(a) is in an unexpanded state. A width (w) of the planar sheet is indicated.

Figure 22:
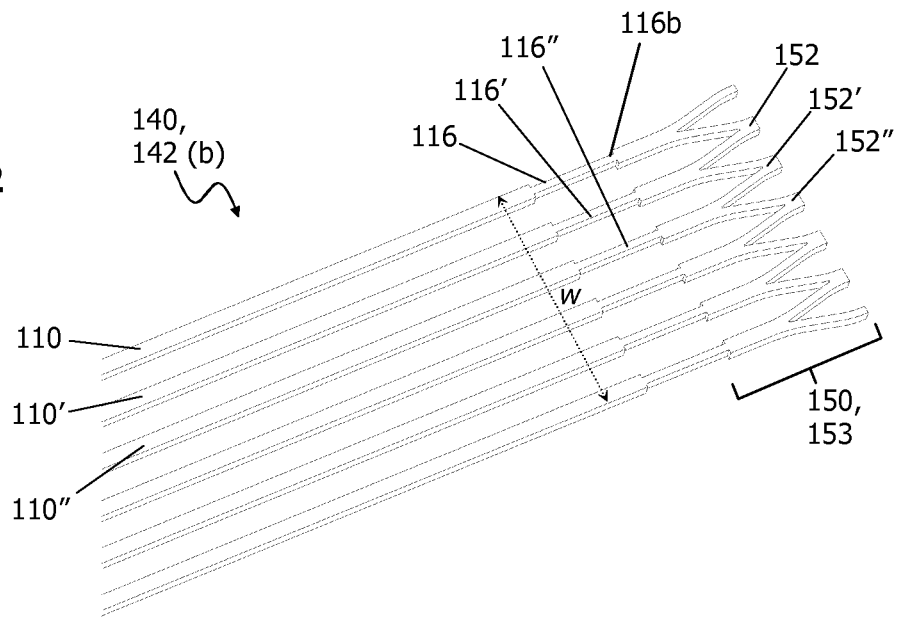
FIG. 22 is an isometric view of an LM assembly, formed by expansion of the expandable LM assembly of FIG. 21.

FIG. 22 is an isometric view of a expandable planar sheet 142(b) expanded to form an LM assembly 140, formed by expansion of the planar sheet 142 of FIG. 21, having a set of LMs 110, 110', 110" arranged mutually parallel, a set of tails 116, 116', 116" arranged mutually parallel and each attached by their trailing ends to an LM 110, 110', 110", and having a common end stop 150, comprising having an undulating form and attached to the leading ends of the tails 116, 116', 116". Specifically, the common end stop is formed from an array of interconnected "Y"s 152, 152', 152" joined by the Y-arms, thus "YYY" in the expanded state. A width (w) of the planar sheet in an unexpanded state is indicated.

The invention claimed is:

1. A mechanical transmission system, MTS, for a steerable tool, which MTS has a proximal end, a distal end, a transmission shaft region, TSR, and transmission bendable distal part (TBDP) adjacent to the TSR that moves omnidirectionally responsive to actuation of the MTS at the proximal end, wherein the MTS comprises:
a set of longitudinal members, LMs, configured to transmit actuating movement along the TSR to the TBDP,
a set of longitudinal member, LM guides for guiding the set of LMs, which LM guide comprises a body having a proximal side, a distal side, and an outside edge, wherein the body of the LM guide comprises a set of channels comprising at least 2 channels arranged around a pattern of a fictive tube, each channel:
passing from the proximal side to the distal side of the body,
configured to retain an LM of the set in a fixed radial position around the pattern of the fictive tube,
being connected to the outside edge of the body via a slot, wherein the slot has a width narrower than the channel width,
wherein each LM is inserted into a channel of the set of channels of an LM guide such that they are arranged around the pattern of the fictive tube in a fixed radial position, and wherein each LM is disposed at one end with a longitudinal tail having a trailing end at one end attached to the LM and at the other end a leading end, wherein at least the trailing end is configured for passage through the slot of the LM guide, wherein the tail leading end is provided with an end stop having a width greater than the channel width to prevent entry of the end stop into the channel.

2. The LM guide according to claim 1, wherein the number of channels is at least 4.

3. The MTS according to claim 2, wherein at least two of the LM guides in the set are articulated LM guides tandemly arranged in the TDBP and are mutually articulated, thereby supporting omnidirectional bending of the LMs in the TDBP.

4. The MTS according to claim 3, wherein the articulated LM guides are in pairwise mutual contact through a pivot joint.

5. The MTS according claim 2, wherein
at least two of the LM guides in the set are fixed LM guides arranged in the TSR and are rotationally fixed with respect to each other, or
only one of the LM guides in the set is a fixed LM guide arranged in the TSR, and having a continuous body spanning the length of the TSR.

6. The MTS according to claim 2, further comprising a transmission bendable proximal part, TBPP, for omnidirectional actuation by the user and which induces the omnidirectional movement response of the TBDP.

7. The MTS according to claim 6, wherein the TBDP is configured for movement in at least two different intersecting planes responsive to the movements of the TBPP, and wherein the MTS is further provided with an end effector at the distal end of the TBDP wherein the MTS is configured such that the end effector is rotationally fixed in relation to the distal bending part TBDP, and the end effector is rotatable when the TBDP is in a bent position, by a complementary rotation of the TBPP.

8. The MTS according to claim 2, wherein the combined transverse profile of the channel and slot in the body of the LM guide is a T-shaped or mushroom-shape.

9. The MTS according to claim 1, wherein the end stop is further configured to limit entry of the tail leading end into the slot.

10. The MTS according to claim 9, wherein the leading ends of at least two tails are connected to a common end stop.

11. The MTS according to claim 1, wherein a non-tailed end of each LM in the set is attached to an anchoring tab configured to limit entry of the LM into the channel of the LM guide.

12. The MTS according to claim 11, wherein the non-tailed ends of at least two LMs are connected to a common anchoring tab.

13. A surgical robot comprising an MTS according to claim 1.

14. A steerable tool comprising an MTS according to claim 1.

15. The steerable tool according to claim 14, wherein the distal end is provided with an end effector that is a gripper, and the proximal end is provided with a handle to steer the tool and to control the gripper.

* * * * *